(12) United States Patent
Meyrat et al.

(10) Patent No.: US 9,192,412 B2
(45) Date of Patent: Nov. 24, 2015

(54) ANCHOR MEMBER FOR VERTEBRAL OSTEOSYNTHESIS EQUIPMENT

(75) Inventors: Richard Meyrat, Dallas, TX (US); Stephane Fuentes, Marseilles (FR)

(73) Assignee: MEDICREA INTERNATIONAL, Neyron (FR)

( * ) Notice: Subject to any disclaimer, the term of this patent is extended or adjusted under 35 U.S.C. 154(b) by 140 days.

(21) Appl. No.: 14/131,041

(22) PCT Filed: Jul. 20, 2012

(86) PCT No.: PCT/IB2012/053717
§ 371 (c)(1),
(2), (4) Date: Jan. 6, 2014

(87) PCT Pub. No.: WO2013/014589
PCT Pub. Date: Jan. 31, 2013

(65) Prior Publication Data
US 2014/0142630 A1    May 22, 2014

(30) Foreign Application Priority Data

Jul. 25, 2011  (FR) .................................... 11 56727

(51) Int. Cl.
*A61B 17/86* (2006.01)
*A61B 17/70* (2006.01)
*A61B 19/00* (2006.01)

(52) U.S. Cl.
CPC ............. *A61B 17/70* (2013.01); *A61B 17/7035* (2013.01); *A61B 17/7041* (2013.01); *A61B 17/8695* (2013.01); *A61B 2019/307* (2013.01)

(58) Field of Classification Search
CPC ............ A61B 17/8605; A61B 17/861; A61B 17/8625; A61B 17/8695; A61B 17/863

USPC .................................. 606/266–269, 301–308
See application file for complete search history.

(56) References Cited

U.S. PATENT DOCUMENTS

| 5,800,435 | A  | * | 9/1998 | Errico et al. ................... 606/261 |
| 6,585,737 | B1 | * | 7/2003 | Baccelli et al. ............... 606/278 |
| 6,709,434 | B1 | * | 3/2004 | Gournay et al. .............. 606/266 |
| 6,887,242 | B2 | * | 5/2005 | Doubler et al. ............... 606/274 |

(Continued)

FOREIGN PATENT DOCUMENTS

EP        0861636        9/1998

*Primary Examiner* — Jerry Cumberledge
*Assistant Examiner* — Stuart S Bray
(74) *Attorney, Agent, or Firm* — Defillo & Associates, Inc.; Evelyn A. Defilló

(57) ABSTRACT

The anchor member (1) includes an anchoring base (2) having a peripheral proximal wall (5) that inwardly delimits a proximal cavity, and a proximal stud (3) including a distal articulation portion (7) received in the proximal cavity, the proximal wall (5) including a peripheral proximal rim (6) ensuring retention of the distal articulation portion (7) in that proximal cavity. According to the invention, the distal articulation portion (7) has a peripheral edge dimensioned to come into the immediate vicinity of the inner surface of the proximal wall (5), and has a convex distal surface (9) whereof the apex is situated substantially at the axis of the proximal stud (3); and the anchor member (1) includes an elastically deformable element (10) placed in the bottom of said proximal cavity, having a curved shape whereof the apex is situated substantially at the axis of the proximal cavity, the surface (9) bearing against this element (10), and the latter being permanently elastically deformed such that it continuously presses the portion (7) against the rim (6).

7 Claims, 2 Drawing Sheets

(56) References Cited

U.S. PATENT DOCUMENTS

| | | | |
|---|---|---|---|
| 6,918,911 B2* | 7/2005 | Biedermann et al. | 606/267 |
| 7,022,122 B2* | 4/2006 | Amrein et al. | 606/266 |
| 7,335,201 B2* | 2/2008 | Doubler et al. | 606/264 |
| 7,678,136 B2* | 3/2010 | Doubler et al. | 606/246 |
| 7,722,654 B2* | 5/2010 | Taylor et al. | 606/287 |
| 7,819,899 B2* | 10/2010 | Lancial | 606/246 |
| 7,828,830 B2* | 11/2010 | Thramann et al. | 606/331 |
| 7,875,060 B2* | 1/2011 | Chin | 606/267 |
| 7,892,266 B2* | 2/2011 | Carli | 606/301 |
| 7,927,359 B2* | 4/2011 | Trautwein et al. | 606/264 |
| 8,057,517 B2* | 11/2011 | Flynn et al. | 606/257 |
| 8,083,775 B2* | 12/2011 | Winslow et al. | 606/264 |
| 8,097,024 B2* | 1/2012 | Winslow et al. | 606/264 |
| 8,267,979 B2* | 9/2012 | Flynn et al. | 606/305 |
| 8,961,568 B2* | 2/2015 | McKinley et al. | 606/267 |
| 2003/0163133 A1* | 8/2003 | Altarac et al. | 606/61 |
| 2004/0225289 A1* | 11/2004 | Biedermann et al. | 606/61 |
| 2005/0096652 A1* | 5/2005 | Burton | 606/61 |
| 2005/0288670 A1* | 12/2005 | Panjabi et al. | 606/61 |
| 2006/0025771 A1* | 2/2006 | Jackson | 606/61 |
| 2006/0052786 A1* | 3/2006 | Dant et al. | 606/61 |
| 2006/0084989 A1* | 4/2006 | Dickinson et al. | 606/61 |
| 2006/0229606 A1* | 10/2006 | Clement et al. | 606/61 |
| 2006/0241600 A1* | 10/2006 | Ensign et al. | 606/61 |
| 2006/0241603 A1* | 10/2006 | Jackson | 606/61 |
| 2006/0241757 A1* | 10/2006 | Anderson | 623/17.11 |
| 2006/0276791 A1* | 12/2006 | Shluzas | 606/61 |
| 2007/0055236 A1* | 3/2007 | Hudgins et al. | 606/61 |
| 2007/0093832 A1* | 4/2007 | Abdelgany | 606/61 |
| 2007/0118123 A1* | 5/2007 | Strausbaugh et al. | 606/61 |
| 2007/0168036 A1* | 7/2007 | Ainsworth et al. | 623/17.13 |
| 2007/0213719 A1* | 9/2007 | Hudgins et al. | 606/61 |
| 2008/0003054 A1* | 1/2008 | Fan | 403/122 |
| 2008/0065073 A1* | 3/2008 | Perriello et al. | 606/61 |
| 2008/0306555 A1* | 12/2008 | Patterson et al. | 606/303 |
| 2008/0312692 A1* | 12/2008 | Brennan et al. | 606/246 |
| 2009/0118772 A1* | 5/2009 | Diederich et al. | 606/301 |
| 2010/0036417 A1* | 2/2010 | James et al. | 606/246 |
| 2010/0100137 A1* | 4/2010 | Justis et al. | 606/308 |
| 2011/0054545 A1* | 3/2011 | Champagne et al. | 606/301 |
| 2011/0077694 A1* | 3/2011 | Biedermann et al. | 606/305 |
| 2011/0087296 A1* | 4/2011 | Reiley et al. | 606/303 |
| 2011/0098755 A1* | 4/2011 | Jackson et al. | 606/305 |
| 2011/0218577 A1* | 9/2011 | Weiman et al. | 606/305 |
| 2011/0224738 A1* | 9/2011 | Sucec et al. | 606/315 |
| 2012/0245704 A1* | 9/2012 | Childs | 623/23.52 |
| 2012/0271364 A1* | 10/2012 | Sharifi-Mehr et al. | 606/305 |
| 2013/0046350 A1* | 2/2013 | Jackson et al. | 606/305 |
| 2013/0184766 A1* | 7/2013 | Black | 606/289 |
| 2014/0012333 A1* | 1/2014 | Tornier et al. | 606/308 |
| 2014/0066991 A1* | 3/2014 | Marik et al. | 606/279 |
| 2014/0128926 A1* | 5/2014 | Pacheco et al. | 606/304 |
| 2014/0188180 A1* | 7/2014 | Biedermann et al. | 606/328 |
| 2014/0228890 A1* | 8/2014 | Raju et al. | 606/270 |
| 2014/0249589 A1* | 9/2014 | Reiley et al. | 606/302 |
| 2015/0045840 A1* | 2/2015 | Vaucher et al. | 606/305 |
| 2015/0134004 A1* | 5/2015 | Ziolo et al. | 606/266 |

* cited by examiner

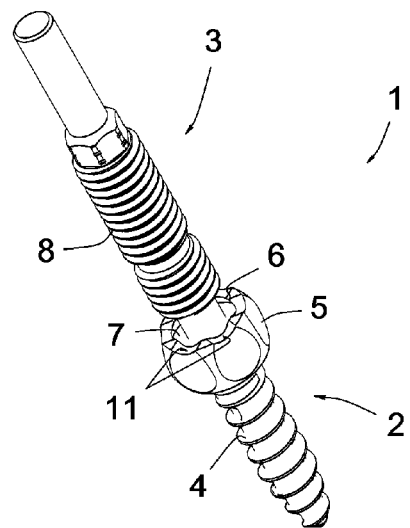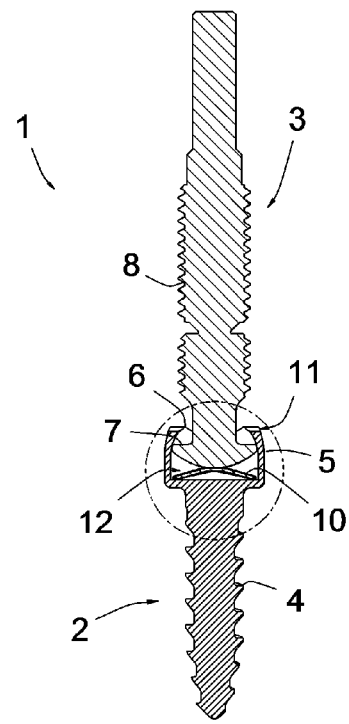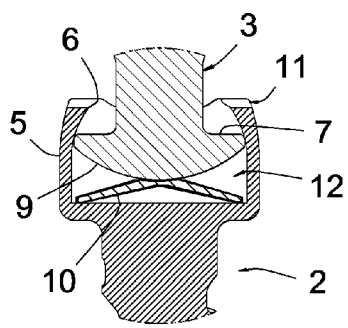
FIG. 1
FIG. 2
FIG. 3
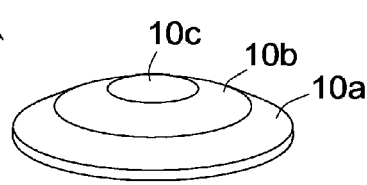
FIG. 4
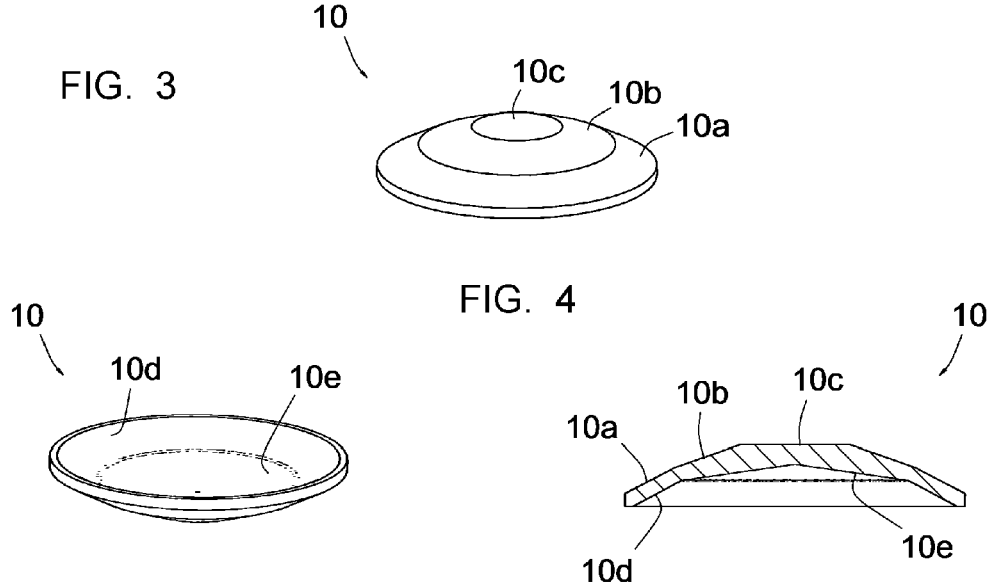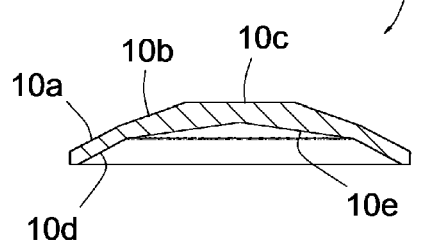
FIG. 5
FIG. 6

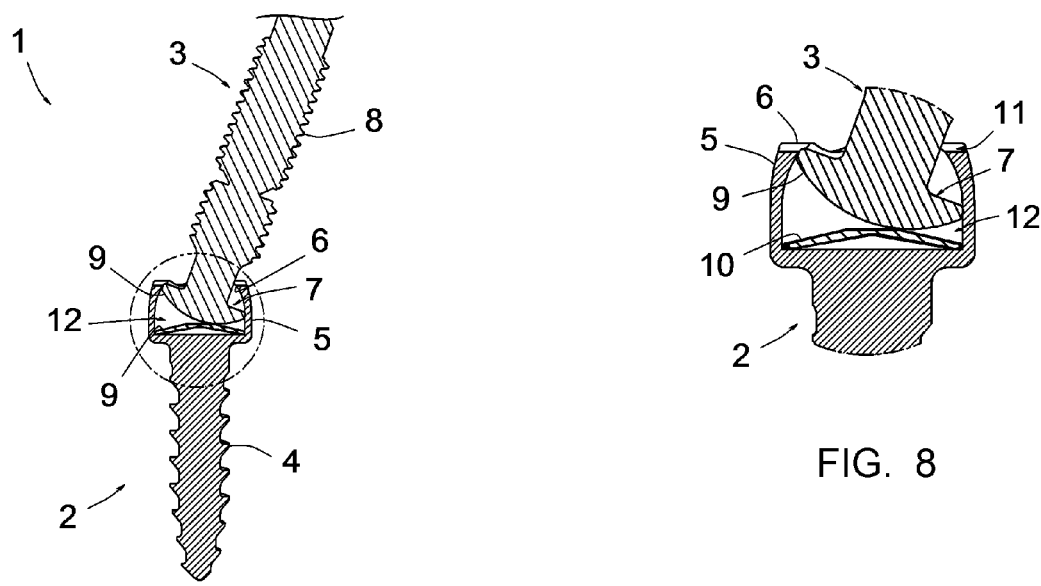
FIG. 7
FIG. 8
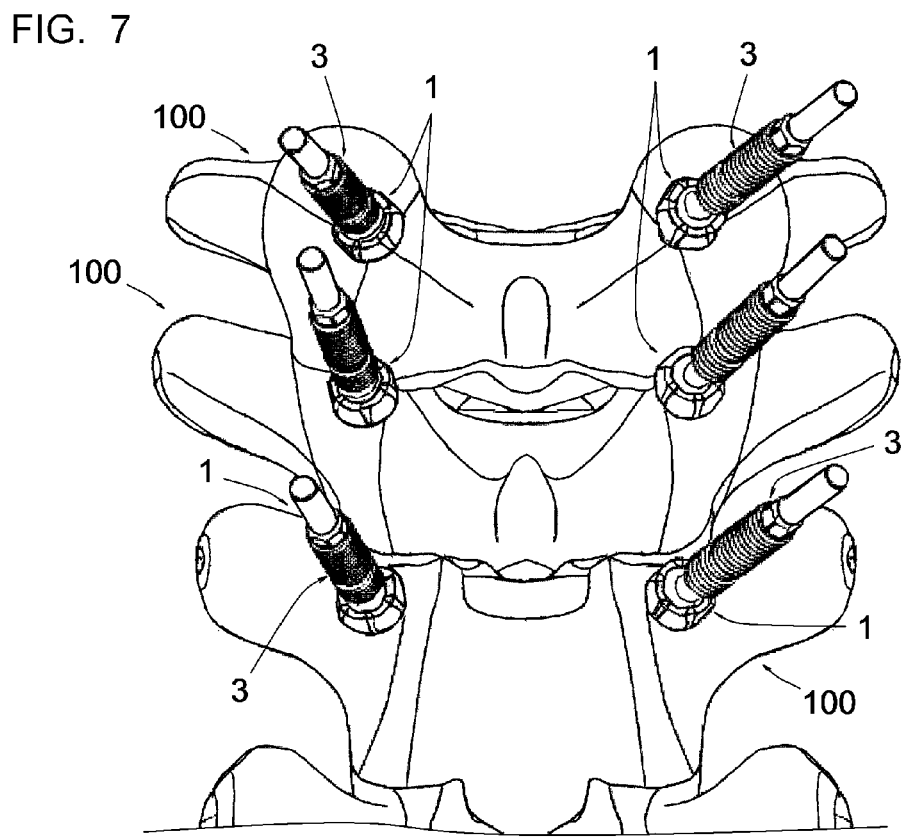
FIG. 9

ANCHOR MEMBER FOR VERTEBRAL OSTEOSYNTHESIS EQUIPMENT

CROSS REFERENCE TO RELATED APPLICATION

This application is a national stage entry of PCT/IB2012/053717 filed Jul. 20, 2012, under the International Convention claiming priority over French Application No. 1156727 filed Jul. 25, 2011.

FIELD OF THE INVENTION

The present invention relates to an anchor member for vertebral osteosynthesis equipment.

BACKGROUND OF THE INVENTION

To immobilize part of the vertebral column, in particular to treat the degeneration of an intervertebral disc, it is well known to use vertebral osteosynthesis equipment comprising anchor members for anchoring to the vertebrae (pedicular screws and/or laminar hooks), connecting rods making it possible to connect said anchor members to one another, and connectors making it possible to connect said connecting rods to said anchor members.

An anchor member is frequently "polyaxial," i.e. comprises a threaded proximal stud articulated relative to an anchoring base, the stud comprising a distal articulation portion and the anchoring base forming a proximal cavity in which said distal articulation portion is received. Patent publication No. EP 0 986 339, in the applicant's name, illustrates an anchor member of this type.

In the known equipment, the proximal studs of the anchor members are, in general, freely movable in the proximal cavities of the anchoring bases, which leads them to adopt by gravity inclined positions relative to the anchoring bases when the anchor members are implanted. These inclined positions are most often bothersome in the implantation site, which is deep and has small dimensions.

The documents US 2003/163133, US 2006/229606, US 2010/100137, EP 0 861 636 and U.S. Pat. No. 5,800,435 show various existing devices that do not resolve this essential drawback.

OBJECTS OF THE INVENTION

The present invention precisely aims to resolve this essential drawback.

SUMMARY OF THE INVENTION

The anchor member to which it relates comprises, in a known manner, an anchoring base including a peripheral proximal wall that inwardly delimits a proximal cavity, and a proximal stud including a distal articulation portion received in said proximal cavity, said proximal wall including a peripheral proximal rim oriented toward the axis of said proximal cavity, ensuring retention of said distal articulation portion in that proximal cavity; said proximal cavity has an axis, said proximal wall has an inner surface on the side of said proximal cavity, and said proximal stud has a longitudinal axis.

According to the invention,
the distal articulation portion has a peripheral edge dimensioned to come into the immediate vicinity of the inner surface of said proximal wall, and has a convex distal surface having an apex, said apex being situated substantially at the longitudinal axis of the proximal stud; and
the anchor member comprises an elastically deformable element placed in the bottom of said proximal cavity, having a curved shape and an apex, said apex of said elastically deformable element being situated substantially at the axis of said proximal cavity, said convex distal surface bearing against said elastically deformable element, and the latter being permanently elastically deformed such that it continuously presses said distal articulation portion against said peripheral proximal rim in order to generate friction between said distal articulation portion and said peripheral proximal rim capable of keeping the proximal stud in a predetermined position without preventing the stud from moving into another position.

Owing to this friction and to the friction exerted between said convex distal surface and said elastically deformable element, the proximal stud keeps its predetermined position, notwithstanding the gravitational force it undergoes, and can be placed in another position, which it will also keep. The convex shape of said distal surface and the curved shape of the elastically deformable element make it possible (i) to obtain a contact surface between the respective apices of said surface and the elastically deformable element remaining substantially situated at the axis of the base, and (ii) to obtain a recess between the periphery of said surface and the periphery of said elastically deformable element, meaning that the periphery of said convex distal surface does not bear against the periphery of the elastically deformable element when the proximal stud is inclined. These conditions are necessary to preserve the incline of the stud.

Said elastically deformable element may be made from a material compressible in the direction of the thickness of that element; preferably, however, said element is formed by a curved wall made from a material that is not compressible in the direction of the thickness of said wall, said element defining:

a peripheral bearing edge intended to bear against the bottom of said proximal cavity,
a hollow surface on one of its sides, intended to be turned toward the bottom of the proximal cavity, and
a protruding surface intended to be turned toward said distal articulation portion.

Said curved wall of the elastically deformable element could be purely bowed, in a spherical dome; according to one possible embodiment of the invention, said curved wall has, on the protruding surface thereof, three successive surfaces separated from one another by marked peripheral edges, i.e. a conical lower surface, a conical median surface whereof the apical angle is greater than that of said lower surface, and an upper central surface perpendicular to the axis of the elastically deformable element.

This faceted form is favorable to perfect operation of the aforementioned curved wall forming the elastically deformable element.

This curved wall can have two successive surfaces on the hollow surface thereof, i.e. a conical lower surface and a conical upper surface whereof the apical angle is greater than that of said conical lower surface.

Said elastically deformable element may be made from any suitable material; when it is formed by said curved wall, it is preferably made from PEEK (polyetheretherketone).

This material is not only perfectly biocompatible, but also has elasticity properties completely adapted to forming said curved wall.

Preferably, the aforementioned peripheral proximal rim of said proximal wall delimiting said proximal cavity is thickened and is curved with the axis of the anchoring base, forming an inner proximal surface at said proximal cavity, curved toward the axis of the anchoring base.

This inner proximal surface allows said distal articulation portion to slide regularly along it when the proximal stud is inclined.

Preferably, the aforementioned peripheral proximal rim of said proximal wall delimiting said proximal cavity has a series of notches capable of partially receiving the proximal stud and thereby allowing increased travel of said proximal stud relative to the anchoring base.

This increased travel is not only favorable in terms of use of the anchor member, but also makes it possible to ensure proper maintenance of the stud in the maximum angulation position.

The invention will be well understood, and other features and advantages thereof will appear, in reference to the appended diagrammatic drawing, showing, as a non-limiting example, one preferred embodiment of the anchor member it concerns.

BRIEF DESCRIPTION OF THE DRAWINGS

FIG. 1 is a perspective view of a proximal stud comprised by said anchor member oriented in the axis of an anchoring base also comprised by said anchor member;

FIG. 2 is a view of the anchor member in axial cross-section;

FIG. 3 is a larger scale view of the details circled in FIG. 2;

FIG. 4 is a perspective enlarged view of an elastically deformable element comprised by the anchor member, showing the outer side of the element;

FIG. 5 is an enlarged perspective view of the elastically deformable element, showing the inner side of the element;

FIG. 6 is a view of the elastically deformable element in diametric cross-section;

FIG. 7 is a view of the anchor member similar to FIG. 2, the proximal stud being inclined relative to the anchoring base;

FIG. 8 is a view of the anchor member similar to FIG. 3, in that same inclined position of the proximal stud; and FIG. 9 is a perspective view of six anchor members implanted in three vertebrae.

FIGS. 1 to 8 illustrate an anchor member 1 that is part of vertebral osteosynthesis equipment, said equipment also, in a well-known manner, comprising connecting rods making it possible to connect several of said anchor members 1 to one another, and connectors making it possible to connect the connecting rods to said anchor members 1.

DESCRIPTION OF THE PREFERRED EMBODIMENTS

The anchor member 1 is of the "polyaxial" type, i.e. it comprises a bone anchoring base 2 and a threaded proximal stud 3, the stud 3 being articulated relative to said base 2. In the illustrated example, the base 2 comprises a threaded body 4 intended to be screwed in the pedicle of a vertebra 100 (cf. FIG. 9); the space 2 could also in particular comprise a laminar hook or a flexible link intended to form a loop around a vertebral lamina or a vertebral apophysis.

The base 2 comprises a head including a proximal wall 5 that inwardly delimits a proximal articulation cavity of the stud 3. This wall has a faceted outer surface, allowing the base 2 to be grasped by a screwing instrument in order to screw said base 2 into the pedicle of a vertebra. It includes a thickened peripheral proximal rim 6 curved toward the axis of the base 2, which ensures retention in said proximal cavity of the distal articulation portion 7. This rim 6 and the wall 5 have a series of eight notches 11 formed in their proximal surfaces, giving them a corrugated outer shape. These notches 11 formed recesses capable of partially receiving a proximal threaded pin 8 comprised by the stud 3. This pin 8 is intended to receive a connector as mentioned above engaged thereon as well as a nut screwed thereon (not shown), for tightening said connector against the wall 5.

The distal articulation portion 7 is received with articular play in said proximal articulation cavity. It has a peripheral edge dimensioned to come into the immediate vicinity of the inner surface of the proximal wall 5, and has a convex distal surface 9 whereof the apex is situated substantially at the axis of the stud 3.

This distal articulation portion 7 is retained in said proximal articulation cavity by said peripheral proximal rim 6, which is, after engagement of the portion 7 in the cavity, fold down toward the axis of the base 2, by deforming the wall 5.

The anchor member 1 also comprises an elastically deformable element 10 placed in the bottom of said proximal cavity, which has a curved shape whereof the apex is situated substantially at the center of said bottom. This element 10 is formed by a curved wall made from PEEK, which defines:
- a peripheral bearing edge against the bottom of said proximal cavity,
- a hollow surface on one of its sides, intended to be turned toward the bottom of said proximal cavity, and
- a protruding surface intended to be turned toward said distal articulation portion 7.

As appears in FIGS. 4 to 6, the element 10 has:
- on its protruding surface, three successive surfaces 10a to 10c separated from one another by marked peripheral edges, i.e. a conical lower surface 10a, a conical median surface 10b whereof the apical angle is larger than that of said lower surface, and an upper central surface 10c perpendicular to the axis of the elastically deformable element 10; and
- on its hollow surface, two successive surfaces 10d, 10e, i.e. a conical lower surface 10d and a conical upper surface 10e whereof the apical angle is greater than that of said conical lower surface 10d.

As shown, said convex distal surface 9 bears against the elastically deformable element 10. The latter is continuously elastically deformed such that it continuously presses the distal articulation portion 7 against the rim 6, so as to generate, between said distal portion 7 and said rim 6, friction capable of keeping the stud 3 in a predetermined position relative to the base 2, without preventing said stud from moving into another position relative to that base 2, by manual pressure exerted on said stud.

When the member 1 is placed, the stud 3 can thus preserve its said predetermined position, notwithstanding the gravitational force it undergoes, and may be placed in another position by manual pressure, which it will also keep. In this way, the studs 3 of the members 1 shown on the left in FIG. 9 are substantially maintained in the axis of the threaded body 4, while the studs 3 of the members 1 shown on the right in FIG. 9 are inclined to the right, thereby freeing the vertebral space situated on the right of the spinal apophyses.

The convex shape of the distal surface 9 and the curved shape of the element 10 simultaneously make it possible to:
- obtain a contact surface between the respective apices of said surface 9 and the element 10 remaining situated substantially at the axis of the base 2, and obtain a recess 12 between the periphery of said surface 9 of the periphery of said element 10, meaning that the periphery of the surface 9 does not bear against the periphery of the element 10 when the stud 3 is inclined.

The faceted shape of the element 10 is favorable to perfect operation of the element, and the increased travel of the stud 3 relative to the base 2, made possible by the notches 11, makes it possible to ensure the proper maintenance of the stud 3 in the maximum regulation position.

The invention consequently provides an anchor member having the decisive advantage of greatly facilitating the implementation of the vertebral osteosynthesis equipment, the proximal studs 3 of a series of placed anchor members 1 not being freely movable in the proximal cavities of the anchoring bases 2, and thus being able to be placed in non-bothersome positions relative to the work in progress on the vertebrae.

The invention has been described above in reference to one embodiment provided as an example. It is of course not limited to that embodiment, but on the contrary encompasses all other embodiments covered by the appended claims.

The invention claimed is:

1. An anchor member for vertebral osteosynthesis equipment, comprising:
   an anchoring base including a peripheral proximal wall that inwardly delimits a proximal cavity, and
   a proximal stud including a distal articulation portion received in said proximal cavity,
   said proximal wall including a peripheral proximal rim oriented toward the axis of said proximal cavity, ensuring retention of said distal articulation portion in that proximal cavity; said proximal cavity has an axis, said proximal wall has an inner surface on a side of said proximal cavity, and said proximal stud has a longitudinal axis;
   wherein:
   the distal articulation portion has a peripheral edge dimensioned to come into the immediate vicinity of the inner surface of said proximal wall, and has a convex distal surface having an apex, said apex being situated substantially at the axis of the proximal stud; and
   the anchor member comprises an elastically deformable element placed in the bottom of said proximal cavity, having a curved shape and an apex, said apex of said elastically deformable element being situated substantially at the axis of said proximal cavity, said convex distal surface bearing against said elastically deformable element, and the latter being permanently elastically deformed such that it continuously presses said distal articulation portion against said peripheral proximal rim in order to generate friction between said distal articulation portion and said peripheral proximal rim capable of keeping the proximal stud in a predetermined position without preventing the stud from moving into another position.

2. The anchor member according to claim 1, wherein said elastically deformable element is formed by a curved wall made from a material that is not compressible in the direction of a thickness of said wall, said element defining:
   a peripheral bearing edge intended to bear against the bottom of said proximal cavity,
   a hollow surface on one of its sides, intended to be turned toward the bottom of the proximal cavity, and
   a protruding surface intended to be turned toward said distal articulation portion.

3. The anchor member according to claim 2, wherein said curved wall of the elastically deformable element has, on the protruding surface thereof, three successive surfaces separated from one another by marked peripheral edges, i.e. a conical lower surface, a conical median surface whereof the apical angle is greater than that of said lower surface, and an upper central surface perpendicular to the axis of the elastically deformable element.

4. The anchor member according to claim 2, wherein said curved wall of the elastically deformable element has two successive surfaces on the hollow surface thereof, i.e. a conical lower surface and a conical upper surface whereof the apical angle is greater than that of said conical lower surface.

5. The anchor member according to claim 2, wherein said curved wall is made from polyetheretherketone.

6. The anchor member according to claim 1, wherein said peripheral proximal rim is thickened and is curved with the axis of the anchoring base, forming an inner proximal surface at said proximal cavity, curved toward the axis of the anchoring base.

7. The anchor member according to claim 1, wherein said peripheral proximal rim has a series of notches capable of partially receiving the proximal stud and thereby allowing increased travel of said proximal stud relative to the anchoring base.

* * * * *